United States Patent [19]

Coelus

[11] 4,359,890

[45] Nov. 23, 1982

[54] APPARATUS FOR TESTING THE LOAD-BEARING PROPERTIES OF A FOUNDATION

[75] Inventor: Gaspar Coelus, Nieuwpoort, Belgium

[73] Assignee: Societe Anonyme France-Atlas, France

[21] Appl. No.: 166,297

[22] Filed: Jul. 7, 1980

[30] Foreign Application Priority Data

Jul. 9, 1979 [FR] France .................................. 79 18176

[51] Int. Cl.³ .............................................. G01N 3/34
[52] U.S. Cl. ............................................ 73/12; 73/84
[58] Field of Search ..................... 73/11, 12, 82, 84, 79

[56] References Cited

U.S. PATENT DOCUMENTS

| | | | |
|---|---|---|---|
| 3,214,966 | 11/1965 | Menzies | 73/84 X |
| 3,557,603 | 1/1971 | Carr | 73/12 |
| 3,946,598 | 3/1976 | Towne et al. | 73/12 |
| 4,116,041 | 9/1978 | Tholen et al. | 73/12 |

FOREIGN PATENT DOCUMENTS 575536 10/1977 U.S.S.R. .................................. 73/84

Primary Examiner—Charles A. Ruehl
Attorney, Agent, or Firm—Robert E. Burns; Emmanuel J. Lobato; Bruce L. Adams

[57] ABSTRACT

Apparatus for testing the load-bearing properties of piles comprises a cover which fits over the upper end of a pile as a cap. A weight slidable on guide posts extending up from the cover is releasably held in a raised position by wedges acting on a bar which is pivotally connected with the weight and extends up through a tapered opening in a transverse support extending between and supported by upper portions of the guide posts. When the weight is released by moving the wedges upwardly in the tapered opening of the support, it falls by gravity toward the pile cover and engages coil springs mounted on the cover. The springs convert the kinetic energy of the weight into potential energy and apply a reaction force through the cover to the pile for a period of time. Acceleration of the pile and of the weight are measured and recorded. The potential energy of the springs is reapplied to the weight to cause it to rebound to a height lower than its initial height where it is held by the wedges. This height is measured. The weight is further raised by jacks to a selected height for a subsequent test.

13 Claims, 3 Drawing Figures

APPARATUS FOR TESTING THE LOAD-BEARING PROPERTIES OF A FOUNDATION

The invention relates to a method and apparatus making it possible to carry out dynamic tests on the loading of foundations.

It relates for example to testing foundation piles, for which it is particularly important to know the load-bearing capacity, i.e. the resistance to being driven into the ground under the action of a vertical force applied to the head of the pile. It also relates to measuring the settling of the piles depending on the loads to which they are subjected.

From these two characteristics one can deduce the admissible operating load, for which one takes a safety coefficient, for example at least equal to 2.5, with respect to the breaking load, as well as the settling of the pile for the operating load which must be compatible with the construction which the piles are intended to support.

It is virtually impossible to determine the load bearing capacity by calculation, to the extent that it depends on numerous parameters linked not solely with the physical characteristics of the pile, but also with those of the ground surrounding the pile. Consequently, this load-bearing capacity is determined by practical tests "in situ," i.e. on the pile which has been driven into the ground in its final location.

Several methods are presently known for determining the load-bearing capacity of a pile and its settling. A first method consists of carrying out a test for the static loading of the pile. According to this method, a weight is placed above the head of the pile by a network of small metal girders and a master girder. Interposed between the master girder and the head of the pile is a hydraulic jack which is provided with a calibrated pressure gauge of which the pressure is varied in stages, in order to exert a progressive force on the head of the pile. The settling of the pile may thus be determined by measurement, the breaking load corresponding to the pressure at which a slight increase causes a sudden increase in the settling.

This static method has numerous drawbacks, in fact it takes a long time to carry out and requires a considerable amount of handling. Furthermore, the weight which it is necessary to place above the pile is considerable, since it may be greater than 2.5 times the operating load. In addition, for large piles, one generally proceeds by extrapolation in order to determine the breaking load, which leads to inaccurate results, hence the necessity of providing very considerable safety margins.

However, it should be noted that this test is well suited to determining the admissible operating load.

Other methods exist for dynamic tests for the loading of a pile, consisting of transmitting a pulse to the head of the pile, by the impact of a tup and of studying the propagation of this pulse along the pile. One dynamic method based on this principle is known by the name "TNO" method. According to this method, a tup of relatively low weight is propelled by means of compressed air in the direction of the head of the pile. This produces a very brief impact and at the time of the impact the tup has a very high speed. It produces in the pile great pressures and great accelerations which are not uniform over the entire pile and which furthermore spread into the ground surrounding the pile. The very considerable deformation energy caused by the falling of the tup causes a vibration in the pile and surrounding ground, which excludes the possibility of linking settling with a static reaction and with a breaking load.

This "TNO" method may be used for the comparison of the load-bearing capacity of different piles, but otherwise requires the calibration of one of the piles by a static test.

This is also the case of tests using measurement of dynamic impedance, consisting of creating and studying a forced vibration in the pile.

One of the aims of the present invention is to propose a method and apparatus for dynamic tests which make it possible to obtain the static load/settling curve directly without reference to a static test.

Another aim of the present invention is to propose a method and apparatus for dynamic tests which eliminate the propagation of a shock wave in the pile and surrounding ground, causing considerable pressures and stresses in the pile.

Another aim of the present invention is to propose a reliable method and apparatus for which the laws of dynamics are applicable.

Further aims and advantages of the present invention will become apparent from the ensuing description which is given solely by way of an example and does not intend to limit the latter.

The method of the dynamic test for loading a pile "in situ" is characterised by the fact that:
- a predetermined quantity of energy is liberated instantaneously in the direction of the pile,
- this energy is accumulated in a resilient manner and the accumulated energy is retransmitted to the head of the pile progressively over a period of time,
- the load applied to the head of the pile and the movement of the latter are measured and calculated at each instant, which makes it possible to deduce the ultimate load-bearing capacity of the pile.

The apparatus for carrying out the method is characterised by the fact that it comprises:
- Means for instantaneously liberating a predetermined quantity of energy in the direction of the pile,
- a damper device interposed between said means and the head of the pile, for accumulating the said quantity of energy and retransmitting it progressively over a period of time to the head of the pile,
- means for measuring and calculating at each instant the load applied to the pile and the movement of the head of the pile.

The invention will be better understood on referring to the ensuing description, and to the accompanying drawings which form an integral part thereof.

FIG. 1A is a schematic diagram of accelerometers and recording equipment.

According to the invention, a predetermined quantity of energy is liberated in the direction of the head of the pile. This energy may be composed for example by the drop of a tup falling from a predetermined height. This energy may thus be in the form of kinetic energy.

This energy is accumulated in a resilient manner and retransmitted progressively in the direction of the head of the pile. This accumulation of energy, then its retransmission, is ensured by a resilient damper member. This damper member shortens when it accumulates energy and resumes its length when it restores this energy.

The resilient damper is able to accumulate the entire quantity of energy which has been liberated in the direction of the pile. Thus, according to the invention, the sudden impact between the tup and the head of the pile is prevented.

The use of the drop of a tup to constitute the predetermined quantity of energy which is liberated in the direction of the pile makes it possible to have a relatively considerable quantity of energy available with regard to moving masses and in particular the mass of the tup. On the other hand, the damper member prevents the phenomenon of sudden impact, such as is produced in dynamic methods which are known and carried out at present.

Moreover, it should be noted that the transmission of accumulated energy by the tup to the pile takes place progressively over a period of time, owing to the damper member, this is contrary to the dynamic methods by which the tup transmits its energy to the pile in a very short time. The energy transmitted to the pile is transformed by compression of the damper member into an increasing force in the pile in order to overcome the resistance of the ground which increases with the settling and a part is used for setting the pile, the testing device and part of the ground adjacent the pile in movement, in a manner which is much slower than a movement using impact. A very small part of the energy is lost in the form of heat losses, frictional losses etc.

The remaining energy, accumulated by the damper member, is restored by the latter to the tup and constitutes part of a new quantity of energy which can be liberated in the direction of the pile for a new test. This part is completed, naturally, in order to constitute this new quantity of energy completely for a new test.

According to the invention, one also measures the parameters which make it possible directly or by calculation to determine in particular the static force to which the pile has been subjected, its settling and its movement. For example, these elements may be accessible by measuring the height from which the tup is released, the acceleration of the tup, the acceleration of the head of the pile and the height to which the tup reascends. The acceleration curves may be recorded and a man skilled in the art will easily discover the elements determining the characteristics of the pile, for example by integration of the curves.

Figure 2:
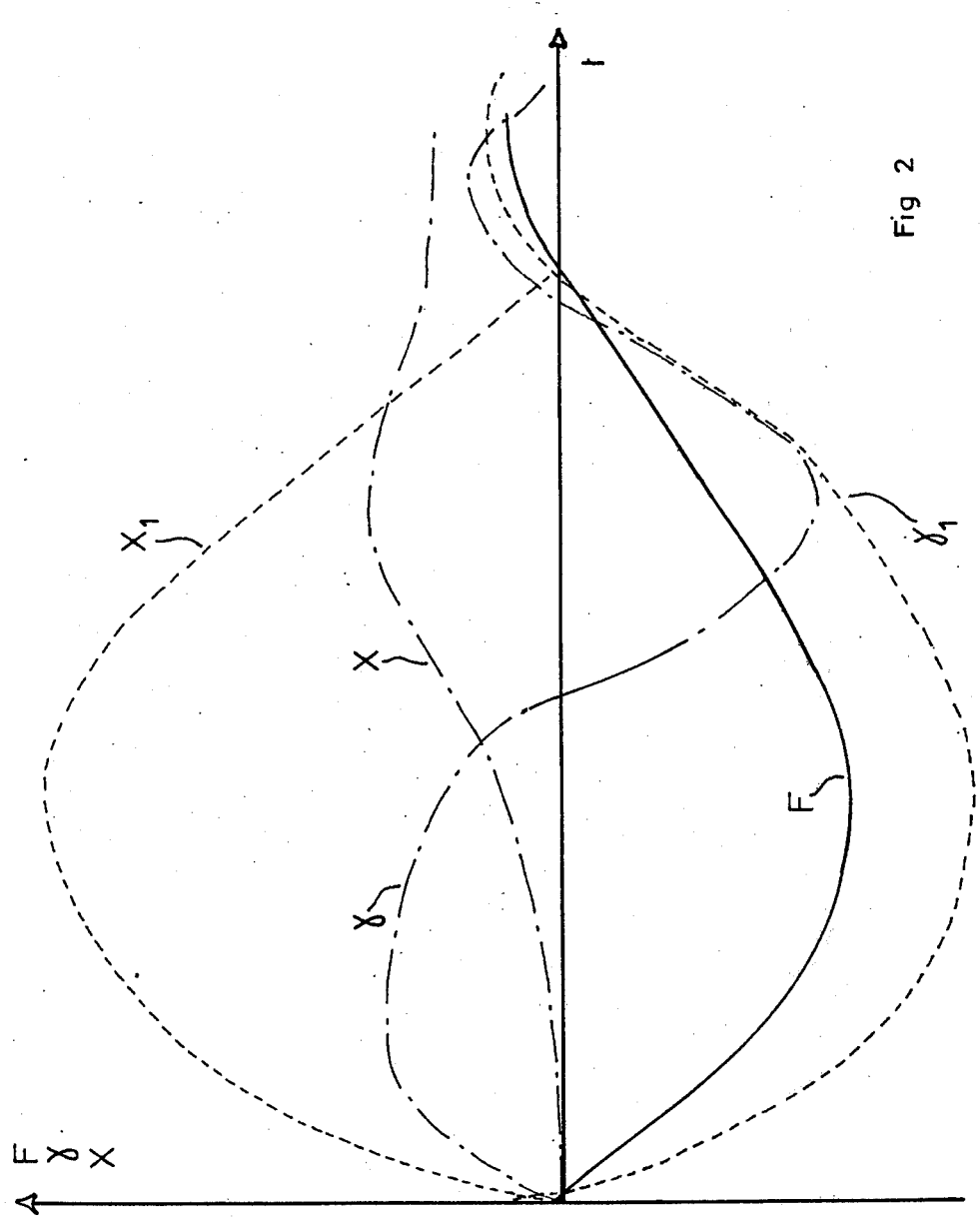
FIG. 2 shows what could be the curve of variations of several parameters either measured, or calculated, as a function of time.

FIG. 2 shows the variations of the load applied to the pile (F), accelerations of the tup ($\gamma_1$ TUP) and of the head of the pile ($\gamma$ HEAD OF THE PILE) as well as the movements of the tup ($X_1$ TUP) and of the head of the pile ($X$ HEAD OF THE PILE). From these curves, it will be easy for a man skilled in the art to deduce the settling of the pile depending on the static load applied and the ultimate load carrying capacity of the pile. In particular, adjacent parts of the various curves $\gamma$ HEAD OF THE PILE and $\gamma_1$ TUP correspond to the simultaneous movement of the tup and of the pile in the ground.

Figure 1:
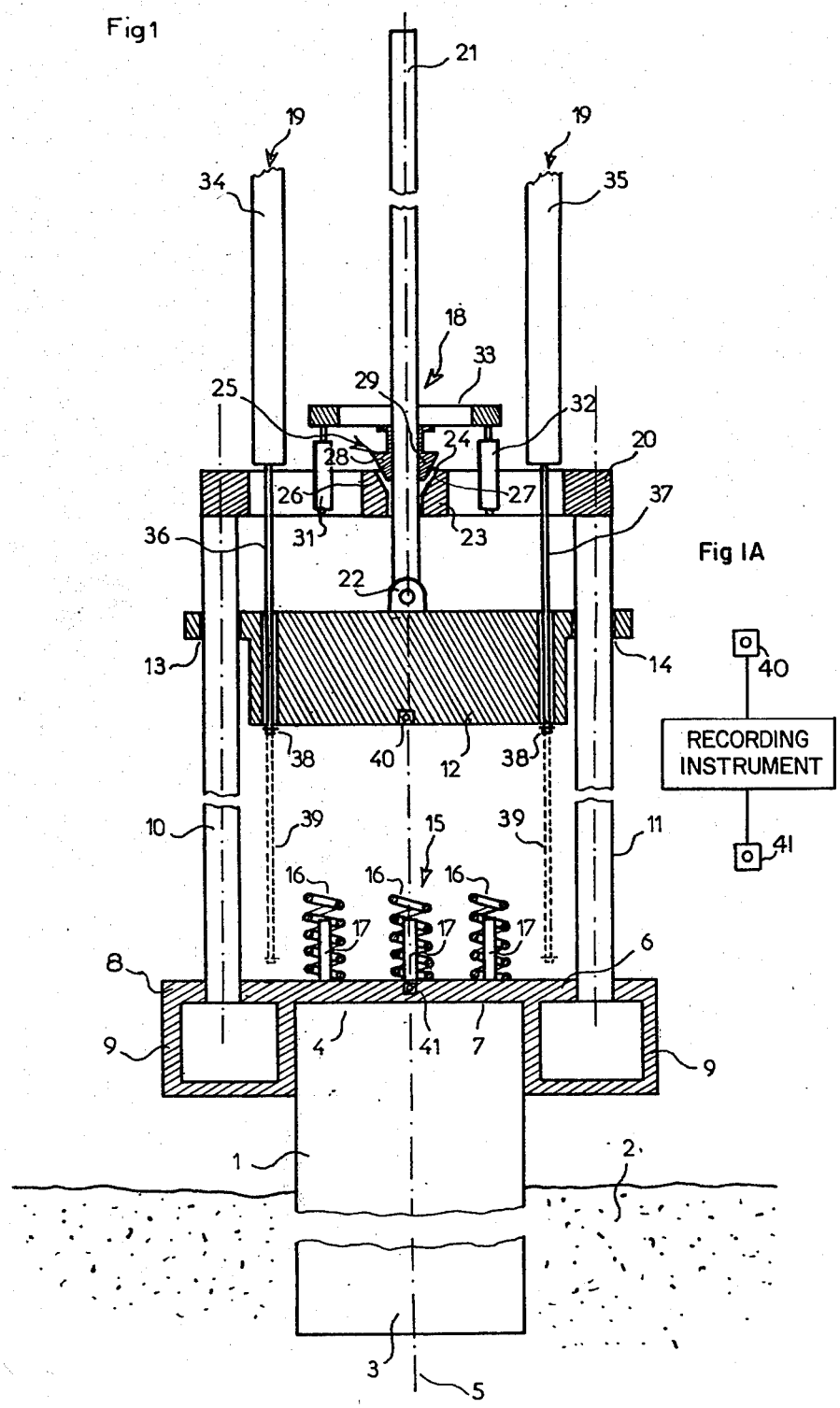
FIG. 1 is an explanatory diagrammatic view of the apparatus for the dynamic testing of piles.

FIG. 1 shows diagrammatically the apparatus according to the invention, for carrying out the method, in a preferred embodiment. As will be apparent from the ensuing description, this apparatus may have numerous variations without diverging from the scope of the invention.

In this figure, the reference numeral 1 firstly designates a rectilinear pile, of any type known per se, driven vertically into the ground 2. The reference numeral 3 designates the tip of the pile, i.e. its lower end located in the ground and the reference numeral 4 designates the head of the pile, i.e. its upper end. Furthermore, the pile has a substantially vertical axis 5. The invention also relates to an inclined pile. Its cross-section may be round, square, rectangular or of any other shape.

The apparatus according to the invention firstly comprises a cover 8, which covers the head of the pile. This cover comprises a base plate 6 which follows the shape of the upper surface 7 of the head 4 of the pile. Advantageously, this upper surface could be prepared before the cover is fitted, by any means within the scope of a man skilled in the art.

Furthermore, the cover comprises rims 9 which follow the shape of the periphery of the pile in the vicinity of its head. The base plate 6 is substantially perpendicular to the axis 5 of the pile, i.e. substantially horizontal in the case of a substantially vertical pile.

Guide means for the tup are connected to the cover 8. These means are composed for example of two posts 10 and 11 located on either side of the axis 5 and parallel to the latter. These two posts facilitate guidance of the tup 12, illustrated in the upper position in FIG. 1. In the vicinity of the guide posts, the tup comprises two orifices 13 and 14, provided in flanges as illustrated in FIG. 1. The posts pass through the orifices, which ensures guidance of the tup by sliding, at the time of its longitudinal vertical movement.

The tup is composed of any suitable material and for example of heavy plates of predetermined weight, of which it is possible to vary the number in order to have a variable weight and in order to adapt the latter to the nature of the pile subjected to the test. A material such as steel is suitable for constructing the tup.

On its upper surface, plumb with the tup, the base plate 6 comprises a damper device 15. According to the invention, numerous types of damper devices are suitable. For example, they may be of the hydraulic, pneumatic or hydro pneumatic type.

In a preferred embodiment, the damper device is composed of a plurality of compression springs 16 arranged in a bank. These springs may also be formed by means of spring washers. According to the embodiment illustrated, the springs have an axis substantially parallel to the axis 5. Preferably, they are guided by rods 17 respectively having a length shorter than the length of the springs when compressed.

These springs are arranged in sets, parallel to each other and several sets may be superimposed preferably by interposing intermediate plates therebetween. Furthermore, in the vicinity of its contact surface with the springs, the tup may have an impact plate intended to protect the latter at the time of the impact with the upper part of the springs.

Furthermore, means make it possible to release and retain the tup at will and means make it possible to raise the tup to the desired height. According to the embodiment illustrated diagrammatically, these means 18 and 19 respectively are supported by a support 20, composed for example of small girders arranged in the vicinity of the upper part of the posts 10 and 11 and connected thereto.

Preferably, the means 18 for releasing and retaining the tup are constituted by a substantially vertical bar 21 which is coaxial with the axis 5. This bar 21 is pivoted at 22 to the upper part of the tup. It passes through the support 20 in the vicinity of a sleeve 23 connected thereto. The sleeve 23 comprises an orifice 24 whereof at least one part, preferably the upper part, is flared upwards. It may have the shape for example of a frustum of a cone or of an inverted frustum of a pyramid. The other part of the orifice 24 has a cross-section substantially equal to the section of the bar 21.

A locking device 25 grips the bar in the orifice 24 of the sleeve 23, by filling the space comprised between the flared shape of the orifice and the bar. For example, in the case of a bar 21 of retangular section, the flared part of the orifice 24 is obtained by the inclination of a part 26 and 27 of two opposite sides of the orifice 24. The locking device is constituted by two wedges 28 and 29, the shape of which enables them to be fitted in the spaces comprised between the inclined sides 26 and 27 of the orifice and the opposing walls of the bar 21.

Locking takes place by conical gripping when the wedges are actuated in a downwards direction and when the tup tends to descend. On the other hand, when the two wedges are actuated in the upwards direction, the bar is unlocked and is able to slide through the orifice 24, thus releasing the tup.

The actuation of the two wedges, or of the locking device is initiated for example by two jacks 31 and 32, having substantially vertical axes, moving a support 33 to which the wedges 28 and 29 are connected, upwards or downwards. It should be noted that the length of the bar 21 is such that the latter remains engaged at least in the locking device when the tup is in the extreme lower position.

The locking device which has been described is in no way limiting. For example, the bar 21 could be replaced by a rack, preferably a double rack, which latches lock or unlock by engaging in its teeth and disengaging therefrom. However, the device composed of the bar 21 and of the two wedges 28 and 29 has the advantage of being self-locking and of locking the tup solely when the latter has a tendency to descend.

According to the embodiment illustrated, the device 19 which makes it possible to raise the tup to the desired height, is composed of two jacks 34 and 35 whereof the body is located above the support 20 and connected thereto. The axis of the two jacks is substantially parallel to the axis 5 of the pile and preferably they are located symmetrically with respect to the axis 5. In a preferred embodiment, their respective rods 36 and 37 pass through the depth of the tup and at their lower end comprise any suitable device 38 for retaining the latter. However, these rods are not connected to the tup and are able to slide in orifices passing through the tup. The broken lines 39 represent the rods in the lower position, the tup being assumed to have been retained in the upper position by the locking device which has been described.

The relative position of the two jacks 34 and 35 as well as of the two guide posts 10 and 11 illustrated in FIG. 1 is not limiting and these different parts could be arranged differently with respect to each other without diverging from the scope of the invention. For example, the two jacks 34 and 35 could be placed respectively at the rear of the guide post 10 and at the front of the guide post 11. The guide posts and the jacks however are symmetrical with respect to the axis 5.

Any suitable device for determining the load transmitted by the tup to the pile and for determining settling of the pile is possible. For example, it is possible to measure the movement of the tup and of the head of the pile by micrometers arranged at suitable points. However, the invention prefers to use two accelerometers of a known type, respectively 40 and 41 located on the one hand on the tup and on the other hand in the vicinity of the cover 5. These accelerometers supply electrical signals depending on the respective acceleration of the tup and of the head of the pile, which could be recorded for example on a high speed magnetic tape or on a recording oscilloscope to which the accelerometers are connected as illustrated schematically in FIG. 1A. In the latter case, advantageously, the curve could be photographed and constitute proof of the test.

It will be easy for a man skilled in the art to choose control members as well as the control logic for the various jacks 34,35,31 and 32 which are preferably hydraulic jacks. Furthermore, it will be easy for him to select processing to which the electrical signals provided by the two accelerometers 40 and 41 are to be subjected, i.e. mainly amplification, in order that these electrical signals can be visualized and calibrated.

The operation of the device according to the invention is as follows. The two rods 36 and 37 of the two jacks 34 and 35 are assumed to be in their lower position 39 shown in broken line. The two wedges 28 and 29 lock the bar 21 in the orifice 24. As for the tup, it is located in the upper position and its height is measured.

In order to carry out the test, the two wedges 28 and 29 are unlocked, thus releasing the tup. As it falls in the direction of the pile, the latter constitutes a quantity of energy determined by the height from which it falls. It then comes into contact with the springs, which it compresses. The latter accumulate the energy constituted by the falling action of the tup and retransmit the latter progressively to the pile. The energy which has not been used is restored by the springs, which results in rebounding of the tup. When the latter has reached a substantially zero speed the two wedges will lock the bar 21 again. The two wedges 28 and 29 may be placed in the locked position before the tup has reached a zero speed, in view of the fact that they exert only a negligible engagement on the bar 21 when the tup is ascending and are only really effective when the tup tends to drop.

The height to which the tup reascends is also measured and from the difference between the height of the fall and the height of the reascent, it is possible to deduce the energy absorbed by the pile. Furthermore, the respective accelerations of the tup and of the head of the pile have been recorded and make it possible to deduce their respective speed and movement by integration. Moreover, it is also possible to deduce from these measurements the load to which the pile is subjected and the settling of the latter.

After the test, the two jacks 34 and 35 come into action and raise the tup to a height corresponding to a predetermined quantity of energy equal to the preceding quantity or to a different quantity depending on each individual case. When the tup is at the desired height, the wedges are locked and the two rods 36 and 37 of the jacks have dropped into their position 39. The device is thus ready for a new test.

From the results of these tests, a man skilled in the art will be able to determine the characteristics of the pile, i.e. its load-bearing capacity and its settling according to the load applied. The invention thus makes it possible to carry out simple and rapid tests. The results obtained are also remarkably reliable and significant.

Naturally, the method and apparatus which have been described may have other embodiments which are not outside the scope of the invention. In particular they may apply to all types of foundations, inclined piles, groups of piles, sole-plates, shafts, wooden piles etc.

What is claimed is:

1. Apparatus for testing the load-bearing properties of a foundation such as a pile, comprising a weight, means for sustaining said weight in a position at an initial height above the foundation, means for releasing said weight to fall by gravity toward the foundation, means for guiding said weight, resilient means interposed between said weight and said foundation, said resilient means being compressed by the kinetic energy of the falling weight and converting such kinetic energy into potential energy while applying a force to said foundation over a period of time, the potential energy of the compressed resilient means being applied to said weight to project said weight upwardly to a second height lower than its initial height, said sustaining means being operative to sustain it at said second height and means for sensing movement of said foundation by force applied through said resilient means.

2. Apparatus according to claim 1, further comprising means for raising said weight from said second height to a selected height for a subsequent test.

3. Apparatus according to claim 2, in which said raising means comprises jack means and means connecting said jack means with said weight to permit free fall of said weight from said initial height to said resilient means.

4. Apparatus according to claim 1, in which said sensing means comprises means for measuring and recording acceleration of said foundation by force applied through said resilient means.

5. Apparatus according to claim 1, further comprising means for measuring and recording acceleration of said weight.

6. Apparatus according to claim 1, further comprising a cover applied as a cap on said foundation, said resilient means being mounted on said cover.

7. Apparatus according to claim 6, in which said guiding means comprises posts extending up from said cover, said weight having portions sliding on and thereby guided by said posts.

8. Apparatus according to claim 7, in which said sustaining means comprises a transverse support extending between and supported by said posts above said weight and having an aperture, a bar extending up from said weight and through said aperture in said support, and means carried by said support for gripping said bar to hold it against downward movement.

9. Apparatus according to claim 6, in which said resilient means comprises a plurality of compression springs on said cover.

10. Apparatus according to claim 1, in which said sustaining means comprises a bar extending up from said weight and means for releasably gripping said bar.

11. Apparatus according to claim 10, in which said gripping means is unidirectional in that it permits upward movement of said weight but restrains downward movement of said weight.

12. Apparatus according to claim 11, in which said sustaining means comprises a support having an aperture through which said bar extends, said aperture having an upwardly flaring portion, and said gripping means comprises wedges movable in said flaring portion to grip said bar by a wedging action.

13. Apparatus according to claim 12, in which said means for releasing said weight comprises means for moving said wedges upwardly to release said bar and thereby release said weight.

* * * * *